(12) United States Patent
Huang

(10) Patent No.: US 10,073,033 B2
(45) Date of Patent: Sep. 11, 2018

(54) ULTRAVIOLET AND HIGH-PERFORMANCE LIQUID CHROMATOGRAPHY METHODS FOR THE EVALUATION OF SUNSCREEN EFFICACY

(75) Inventor: Zhen Huang, Marietta, GA (US)

(73) Assignee: SeNA Research, Inc., Marietta, GA (US)

( * ) Notice: Subject to any disclaimer, the term of this patent is extended or adjusted under 35 U.S.C. 154(b) by 0 days.

(21) Appl. No.: 13/823,028

(22) PCT Filed: Sep. 13, 2011

(86) PCT No.: PCT/US2011/051448
§ 371 (c)(1),
(2), (4) Date: Mar. 13, 2013

(87) PCT Pub. No.: WO2012/037158
PCT Pub. Date: Mar. 22, 2012

(65) Prior Publication Data
US 2013/0183765 A1    Jul. 18, 2013

Related U.S. Application Data

(60) Provisional application No. 61/382,154, filed on Sep. 13, 2010.

(51) Int. Cl.
| | |
|---|---|
| G01N 21/33 | (2006.01) |
| G01N 21/63 | (2006.01) |
| G01N 30/06 | (2006.01) |
| C12Q 1/6883 | (2018.01) |
| G01N 30/88 | (2006.01) |

(52) U.S. Cl.
CPC .......... *G01N 21/631* (2013.01); *G01N 21/33* (2013.01); *G01N 30/06* (2013.01); *C12Q 1/6883* (2013.01); *C12Q 2523/313* (2013.01); *C12Q 2525/313* (2013.01); *G01N 2030/8827* (2013.01); *Y10T 436/143333* (2015.01)

(58) Field of Classification Search
CPC ...... G01N 21/631; G01N 21/63; G01N 21/62; G01N 21/00; G01N 21/33; G01N 21/31; G01N 21/25; G01N 30/06; G01N 30/04; G01N 30/02; C12Q 1/6883; C12Q 1/6876; C12Q 1/68
USPC .................. 436/94, 93, 91; 422/631, 63, 62
See application file for complete search history.

(56) References Cited

U.S. PATENT DOCUMENTS

| | | | |
|---|---|---|---|
| 5,691,158 A * | 11/1997 | Reece | G01N 33/5008 250/493.1 |
| 6,410,333 B1 * | 6/2002 | Rouabhia et al. | 436/63 |
| 2003/0152656 A1 * | 8/2003 | Pinnell et al. | 424/769 |

OTHER PUBLICATIONS

Kumari et al, DNA Damage: Detection Strategies, EXCLI Journal, 2008, 7, pp. 44-62.*

(Continued)

*Primary Examiner* — Christine T Mui
(74) *Attorney, Agent, or Firm* — Merchant & Gould

(57) ABSTRACT

Disclosed are compositions which can mimic DNA and/or RNA in cells of a subject and methods of using them as a substrate in testing efficacy of one or more compositions in reducing and/or preventing radiation, such as ultraviolet (UV) radiation-caused DNA and/or RNA damage of said subject. Also disclosed are systems related to the disclosed methods.

3 Claims, 4 Drawing Sheets

(56) References Cited

OTHER PUBLICATIONS

Ravanat Jean-Luc, Direct and indirect effects of UV radiation on DNA and its components, Journal of Photochemistry and Photobiology B: Biology, 2001, 63, pp. 88-102.*

* cited by examiner

ULTRAVIOLET AND HIGH-PERFORMANCE LIQUID CHROMATOGRAPHY METHODS FOR THE EVALUATION OF SUNSCREEN EFFICACY

CROSS-REFERENCE TO RELATED APPLICATIONS

This application is a U.S. National Stage Application under 35 U.S.C. § 371 of International Application No. PCT/US2011/051448 filed Sep. 13, 2011, which claims benefit of U.S. Provisional Application No. 61/382,154 filed Sep. 13, 2010, the contents of which are incorporated herein in their entirety by this reference.

BACKGROUND

Sunlight plays many important roles for all organisms. Appropriate dosage of sunlight has tremendous biological benefits, such as photosynthesis in plants and vitamin $D_3$ production in human skin [Nemanic M K, Whitney J, Arnaud S, Herbert S, Elias P M. Vitamin D3 production by cultured human keratinocytes and fibroblasts. Biochem Biophys Res Commun 1983; 115:444-50; Holick M F. Sunlight and vitamin D for bone health and prevention of autoimmune diseases, cancers, and cardiovascular disease. Am J Clin Nutr 2004; 80:1678S-88S], especially from exposure to ultraviolet (UV) B radiation. However, overexposure to sunlight will have devastating effects, such as cancer formation [Marrot L, Meunier J R. Skin DNA photodamage and its biological consequences. J Am Acad Dermatol 2008; 58(Suppl):S139-48.], on human beings. Sunlight can cause DNA damage and gene mutation that leads to cancer formation, most typically skin cancer. There are many types of DNA lesions, including the cis-syn, trans-syn, (6-4), and Dewar pyrimidine-pyrimidine photolesions [Taylor J-S. Unraveling the molecular pathway from sunlight to skin cancer. Acc Chem Res 1994; 27:76-82]. Among these possible pyrimidine nucleotide lesions, cis-syn and 6-4 photolesions are commonly observed [Taylor J-S, Cohrs M P. DNA, light and Dewar pyrimidinones: the structure and biological significance of TpT3. J Am Chem Soc 1987; 109:2834-5; Douki T, Court M, Cadet J. Electrospray-mass spectrometry characterization and measurement of far-UV-induced thymine photoproducts. J Photochem Photobiol B 2000; 54:145-54; Rochette P J, Therrien J P, Drouin R, Perdiz D, Bastien N, Drobetsky E A, et al. UVA-induced cyclobutane pyrimidine dimers form predominantly at thymine-thymine dipyrimidines and correlate with the mutation spectrum in rodent cells. Nucleic Acids Res 2003; 31:2786-94]. Furthermore, the pyrimidine (6-4) pyrimidone photolesion is very mutagenic [Glas A F, Schneider S, Maul M J, Hennecke U, Carell T. Crystal structure of the T(6-4)C lesion in complex with a (6-4) DNA photolyase and repair of UV-induced (6-4) and Dewar photolesions. Chemistry 2009; 15:10387-96; Thomas M, Guillaume D, Fourrey J L, Clivio P. Further insight in the photochemistry of DNA: structure of a 2-imidazolone (5-4) pyrimidone adduct derived from the mutagenic pyrimidine (6-4) pyrimidone photolesion by UV irradiation. J Am Chem Soc 2002; 124:2400-1; Young A R, Chadwick C A, Harrison G I, Hawk J L, Nikaido O, Potten C S. The in situ repair kinetics of epidermal thymine dimers and 6-4 photoproducts in human skin types I and II. J Invest Dermatol 1996; 106:1307-13], thereby leading to cancer formation.

Skin cancer is currently the most common type of human cancer in the United States [Jung S K, Lee K W, Byun S, Kang N J, Lim S H, Heo Y S, et al. Myricetin suppresses UVB-induced skin cancer by targeting Fyn. Cancer Res 2008; 68:6021-9]. Because DNA damage usually leads to cancer, tremendous attention has been given to damaged DNA repair research [Young A R, Chadwick C A, Harrison G I, Hawk J L, Nikaido O, Potten C S. The in situ repair kinetics of epidermal thymine dimers and 6-4 photoproducts in human skin types I and II. J Invest Dermatol 1996; 106:1307-13; Shimura T, Martin M M, Torres M J, Gu C, Pluth J M, DeBernardi M A, et al. DNA-PK is involved in repairing a transient surge of DNA breaks induced by deceleration of DNA replication. J Mol Biol 2007; 367:665-80; Ueta E, Sasabe E, Yang Z, Osaki T, Yamamoto T. Enhancement of apoptotic damage of squamous cell carcinoma cells by inhibition of the mitochondrial DNA repairing system. Cancer Sci 2008; 99:2230-7; Brissett N C, Doherty A J. Repairing DNA double-strand breaks by the prokaryotic non-homologous end-joining pathway. Biochem Soc Trans 2009; 37:539-45]. In addition to endogenous DNA repair systems, DNA damage prevention, such as protection from UV radiation, can greatly minimize cancer formation. In general, skin application of sunscreen products, which block the UV from sunlight that causes the DNA damage, can effectively minimize DNA photolesion formation and prevent human skin cancer development. Many medical agencies have also recommended the use of sunscreens to temporarily protect the skin from sunlight exposure [Autier P, Boniol M, Dore J F. Sunscreen use and increased duration of intentional sun exposure: still a burning issue. Int J Cancer 2007; 121:1-5; Sayre R M, Dowdy J C, Lott D L, Marlowe E. Commentary on 'UVB-SPF': the SPF labels of sunscreen products convey more than just UVB protection. Photodermatol Photoimmunol Photomed 2008; 24:218-20].

To evaluate the effectiveness of sunscreen products, human subjects are normally used. Measurements of sunscreen effectiveness are performed by administering different sunscreen dosages to volunteers and then exposing them to sunlight [Young A R, Chadwick C A, Harrison G I, Hawk J L, Nikaido O, Potten C S. The in situ repair kinetics of epidermal thymine dimers and 6-4 photoproducts in human skin types I and II. J Invest Dermatol 1996; 106:1307-13; Jung S K, Lee K W, Byun S, Kang N J, Lim S H, Heo Y S, et al. Myricetin suppresses UVB-induced induced skin cancer by targeting Fyn. Cancer Res 2008; 68:6021-9; Young A R, Potten C S, Chadwick C A, Murphy G M, Hawk J L, Cohen A J. Photoprotection and 5-MOP photochemoprotection from UVR-induced DNA damage in humans: the role of skin type. J Invest Dermatol 1991; 97:942-8; Bissonnette R, Allas S, Moyal D, Provost N. Comparison of UVA protection afforded by high sun protection factor sunscreens. J Am Acad Dermatol 2000; 43:1036-8; Young A R, Sheehan J M, Chadwick C A, Potten C S. Protection by ultraviolet A and B sunscreens against in situ dipyrimidine photolesions in human epidermis is comparable to protection against sunburn. J Invest Dermatol 2000; 115:37-41; Wagner J K, Parra E J, L Norton H, Jovel C, Shriver M D. Skin responses to ultraviolet radiation: effects of constitutive pigmentation, sex, and ancestry. Pigment Cell Res 2002; 15: 385-90; Kelly D A, Seed P T, Young A R, Walker S L. A commercial sunscreen's protection against ultraviolet radiation-induced immunosuppression is more than 50% lower than protection against sunburn in humans. J Invest Dermatol 2003; 120: 65-71; Dupuy A, Dunant A, Grob J J. Randomized controlled trial testing the impact of high-protection sunscreens on sunexposure behavior. Arch Dermatol 2005; 141:950-6; Moyal D D, Fourtanier A M. Broad-spectrum sunscreens provide better protection from solar ultraviolet-simulated radiation and natural sunlight-induced immunosuppression in human beings. J Am Acad Dermatol 2008; 58(Suppl): S149-54]. This strategy is costly and allows for difficulty in generalizability because of age, sex, and race differences among the subjects. It is also difficult to cross-validate the quality and effectiveness of different sunscreen products. Moreover, with the traditional methods, it is difficult to develop highthroughput screening for highly efficient and less toxic sunscreens, which are needed to reduce cancer formation, especially skin cancer formation. Unfortunately, there is no simple, efficient, and quantitative methodology to address these cross-validation, high-throughput, and effectiveness questions using sunscreen products with human or animal subjects [Diffey B L, Tanner P R, Matts P J, Nash J F. In vitro assessment of the broad-spectrum ultraviolet protection of sunscreen products. J Am Acad Dermatol 2000; 43:1024-35; Wang S Q, Stanfield J W, Osterwalder U. In vitro assessments of UVA protection by popular sunscreens available in the United States. J Am Acad Dermatol 2008; 59:934-42].

Therefore, there is a need existing for the development of simple, convenient, efficient, effective, inexpensive, and/or quantitative systems and methods to evaluate the sunscreen efficacy.

SUMMARY

Disclosed are methods comprising the steps of: (a) providing an ultraviolet radiation (UV); (b) providing one or more radiation diagnostic compositions representing and/or mimicking DNA in cells of a subject; (c) exposing said radiation diagnostic composition to said UV which passes through one or more protection compositions where said protection composition is positioned between said radiation diagnostic composition and said UV; and (d) analyzing DNA damage of said radiation diagnostic composition.

Also disclosed are systems comprising: (a) a first device to generate ultraviolet radiation; (b) a second device to hold one or more protection compositions; (c) a third device to contain one or more radiation diagnostic compositions representing and/or mimicking DNA in cells of a subject; and (d) a fourth device to analyze DNA damage of said radiation diagnostic composition; wherein said second device is interposed between said first device and said third device, and said third device is interposed between said second device and said fourth device.

Further disclosed are radiation diagnostic compositions comprising one or more single nucleoside and/or single nucleotide in deoxy- and/or ribo-series and/or deoxy-ribo hybrids where the heterocyclic amine base is A, G, C, U or T, one or more dinucleotide in deoxy- and/or ribo-series where the heterocyclic amine base of each of the nucleotide of the dinucleotide is independently selected from a group consisting of A, G, C, U and T, one or more oligonucleotides in deoxy- and/or ribo-series where the number of the nucleotide (nt) forming the oligonucleotide is from 3 to 100 and where the heterocyclic amine base of each of the nucleotide of the oligonucleotide is independently selected from a group consisting of A, G, C, U and T, an artificial skin culture, or a combination of the same, which is/are dissolved in a suitable solvent with a suitable concentration.

BRIEF DESCRIPTION OF THE DRAWINGS

The accompanying drawings, which are incorporated in and constitute a part of this specification, illustrate several forms and together with the description illustrate the disclosed compounds and methods.

DETAILED DESCRIPTION

Before the present compounds, compositions, articles, devices, systems, and/or methods are disclosed and described, it is to be understood that they are not limited to specific synthetic methods or specific treatment methods unless otherwise specified, or to particular reagents unless otherwise specified, as such may, of course, vary. It is also to be understood that the terminology used herein is for the purpose of describing particular forms only and is not intended to be limiting.

UVB sun protection factor (SPF) is normally assigned to different sunscreens products according to their sun protection effectiveness as determined by complicated strategies

Figure 1:
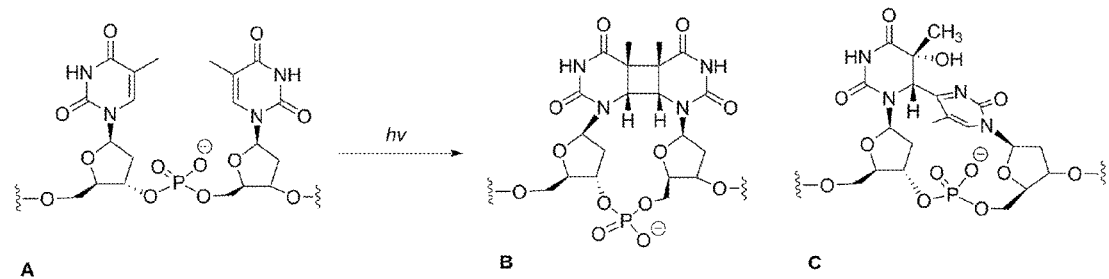
FIG. 1 shows that thymidine-thymidine (TT) dinucleotide is sensitive to UV irradiation where various photolesions are formed under the UV irradiation. Structures of native and damaged thymidine-thymidine (TT) dinucleotides: Native TT dinucleotide (A), cis-syn photolesion (B), and (6-4) photolesion (C).

[systems and methods; Bissonnette R, Allas S, Moyal D, Provost N. Comparison of UVA protection afforded by high sun protection factor sunscreens. J Am Acad Dermatol 2000; 43:1036-8; Wang S Q, Stanfield J W, Osterwalder U. In vitro assessments of UVA protection by popular sunscreens available in the United States. J Am Acad Dermatol 2008; 59:934-42; Hexsel C L, Bangert S D, Hebert A A, Lim H W. Current sunscreen issues: 2007 Food and Drug Administration sunscreen labeling recommendations and combination sunscreen/insect repellent products. J Am Acad Dermatol 2008; 59:316-23]. Because of consumer confusion about the rating of SPF numbers (sunscreen labels), consumer sunscreen SPF labeling is limited to SPF 50+ (ie, SPF≥60) in the European Union (countries). In 2007, the US Food and Drug Administration also proposed a similar grading system for UVB protection with SPF up to 50+, and 4-star grading for UVA protection [Hexsel C L, Bangert S D, Hebert A A, Lim H W. Current sunscreen issues: 2007 Food and Drug Administration sunscreen labeling recommendations and combination sunscreen/insect repellent products. J Am Acad Dermatol 2008; 59:316-23; Osterwalder U, Herzog B. Sun protection factors: world wide confusion. Br J Dermatol 2009; 161(Suppl):13-24]. Because thymidine-thymidine (TT) dinucleotide (FIG. 1) is sensitive to UV irradiation [Blagoev K B, Alexandrov B S, Goodwin E H, Bishop A R. Ultraviolet light induced changes in DNA dynamics may enhance TT-dimer recognition. DNA Repair (Amst) 2006; 5:863-7; Rycyna R E, Alderfer J L. UV irradiation of nucleic acids: formation, purification and solution conformational analysis of the '6-4 lesion' of dTpdT. Nucleic Acids Res 1985; 13:5949-63], and it forms various photolesions (including the deadly 6-4 photolesion), disclosed are simple methods using, in vitro nucleic acid molecules, such as a TT dinucleotide, radiation production and spectrophotometry, such as UV spectrophotometry and analytical machinery, and high performance liquid chromatography (HPLC) analysis to address those validation and effectiveness challenges in the evaluation of sunscreen efficacy and to face the challenges of using human or animal subjects. Also disclosed are UV-HPLC systems that allow easy monitoring of the formation of various photolesions formed during the UV irradiation, for example, the thymidine (6-4) photolesion (pyrimidine(6-4) pyrimidone photoproduct), which is very mutagenic and has characteristic absorption at 320 nm. The disclosed systems can be combined with traditional components of a synthetic TT dinucleotide (mimic of photosensitive DNA) and UV lamp (mimic of sunlight) to analyze commercially available sunscreens.

The disclosed methods and systems are simple sunscreen-analysis methods and systems, which are designed using nucleic acids, such as thymidinethymidine dinucleotides, ultraviolet spectrophotometer or highperformance liquid chromatography, or ultraviolet spectrophotometer and high performance liquid chromatography, avoids the use of human subjects to analyze the effectiveness of sunscreens. The disclosed radiation, such as ultraviolet and/or high-performance liquid chromatography methods and systems, can directly monitor types of DNA photolesions that are formed. To help prevent skin cancer caused by sunlight, the disclosed sunscreen-analysis methods and system provide assistance in choosing the most effective sunscreens for the skin health of consumers.

Methods

Disclosed are methods comprising the steps of: (a) providing a radiation, such as an ultraviolet radiation (UV); (b) providing one or more radiation diagnostic compositions representing and/or mimicking DNA in cells of a subject; (c) exposing said radiation diagnostic composition to said UV which passes through one or more protection compositions where said protection composition is positioned between said radiation diagnostic composition and said radiation, such as UV; and (d) analyzing DNA damage of said radiation diagnostic composition. In some forms, disclosed are methods which further comprise the step of comparing results obtained from step (d) with one or more control samples where said radiation diagnostic composition is exposed to said UV directly without the presence of said protection composition.

In some other forms, disclosed are methods which further comprise the step of identifying a protection composition that reduces and/or prevents ultraviolet (UV) radiation-caused DNA damage in a subject. In some forms, disclosed are methods wherein the step of identifying comprises assaying the presence of mutations in said radiation diagnostic composition. In some other forms, disclosed are methods which further comprise the step of screening efficacy of one or more protection compositions in reducing and/or preventing ultraviolet (UV) radiation-caused DNA damage in a subject.

In some other forms, disclosed are methods wherein said protection composition is sunscreen formulation, cosmetic formulation or a combination of sunscreen formulation and cosmetic formulation. In some other forms, disclosed are methods wherein said step (d) comprises performing the analysis of DNA damage by ultraviolet spectrophotometer, High-performance liquid chromatography (HPLC), or a combination of said ultraviolet spectrophotometer and said HPLC.

In some forms, disclosed are methods wherein said radiation diagnostic composition comprises one or more single nucleoside and/or single nucleotide in deoxy- and/or ribo-series where the heterocyclic amine base is A, G, C, U or T, one or more dinucleotide in deoxy- and/or ribo-series where the heterocyclic amine base of each of the nucleotide of the dinucleotide is independently selected from a group consisting of A, G, C, U and T, one or more oligonucleotides in deoxy- and/or ribo-series where the number of the nucleotide (nt) forming the oligonucleotide is from 3 to 100 and where the heterocyclic amine base of each of the nucleotide of the oligonucleotide is independently selected from a group consisting of A, G, C, U and T, an artificial skin culture, or a combination of the same.

In some other forms, disclosed are methods wherein said radiation diagnostic composition comprises one or more dinucleotides in deoxy- and/or ribo-series, and/or deoxy-ribo hybrids. Said dinucleotide comprises thymidine-thymidine (TT), thymidine-cytidine (TC), thymidine-guanosine (TG), thymidine-adenosine (TA), thymidine-uridine (TU), uridine-uridine (UU], uridine-thymidine (UT), cytidine-cytidine (CC), cytidine-adenosine (CA), guanosine-guanosine (GG), guanosine-adenosine (GA), adenosine-adenosine (AA), or adenosine-cytidine (AC) dinucleotide.

In other forms, disclosed are methods wherein said radiation diagnostic composition is dissolved in a solvent. In some forms, said solvent comprises water, acetonitrile, or a mixture of water and acetonitrile. In other forms, said solvent is a mixture of water and acetonitrile and the volume ratio between water and acetonitrile is from about 1:20 to about 20:1. In still some other forms, said volume ratio between water and acetonitrile is from about 1:9 to about 9:1.

In some forms, disclosed are methods wherein said radiation diagnostic composition is exposed to said UV from about 1 minute to about 48 hours. In some other forms, disclosed are methods wherein said radiation diagnostic composition is exposed to said UV about 5 minutes, 10 minutes, 20 minutes, 30 minutes, 45 minutes, 60 minutes, 90 minutes, 120 minutes, 180 minutes or 240 minutes. In some forms, disclosed are methods wherein said radiation diagnostic composition is dissolved in a solvent with a concentration of from about 0.000001 mmol/L to about 10 mmol/L. In some other forms, said radiation diagnostic composition is dissolved in a solvent with a concentration of from about 0.001 mmol/L to 0.5 mmol/L.

In some forms, disclosed are methods wherein said protection composition is provided in an amount of from about 0.01 mg to about 50 g. In some other forms, said protection composition is provided and/or applied directly on a surface in an amount of from about 2 mg to about 200 mg. In some other forms, said protection composition is directly applied on a transparent surface (or support) that is placed between said radiation diagnostic composition and said UV. In some other forms, disclosed are methods wherein said protection composition is dissolved in a solvent. In some forms, disclosed are methods wherein said solvent comprises water, petroleum ether, or a mixture of water and petroleum ether. In some other forms, disclosed are methods wherein said mixture of water and petroleum ether has a volume ratio between water and petroleum ether from about 1:20 to about 20:1. In other forms, disclosed are methods wherein said protection composition is dissolved in a solvent with a concentration of from about 0.01 mg/mL to about 1000 mg/mL. In other forms, said protection composition is dissolved in a solvent with a concentration of from about 1 mg/ml to about 500 mg/ml. In still some other forms, said protection composition is dissolved in a solvent with a concentration of from about 50 mg/ml to about 200 mg/ml.

In some forms, disclosed are methods wherein said protection composition is a sunscreen formulation. In other forms, disclosed are methods wherein said sunscreen formulation has a sun protection factor (SPF) of from about 10 to about 100. In still some other forms, disclosed are methods wherein said sunscreen formulation has a SPF of about 15, 30, 45, or 70.

In some forms, disclosed are methods wherein said DNA damage comprises formation of DNA lesion. In other forms, disclosed are methods wherein said DNA lesion comprises cis-syn, trans-syn, TT pyrimidine (6-4) pyrimidone, Dewar pyrimidine-pyrimidine photolesion, or a mixture of the same. In still other forms, disclosed are methods wherein said DNA lesion comprises TT pyrimidine (6-4) pyrimidone photolesion.

In some forms, disclosed are methods wherein analysis of said DNA damage of said radiation diagnostic composition is conducted by monitoring the amount of TT pyrimidine (6-4) pyrimidone photolesion formed in said radiation diagnostic composition after said radiation diagnostic composition is exposed to UV for a predetermined period of time. In other forms, disclosed are methods wherein analysis of said DNA damage of said radiation diagnostic compositions is conducted by monitoring the amount of TT dinucleotide preserved in said radiation diagnostic composition after said radiation diagnostic composition is exposed to UV for a predetermined period of time. In some forms, disclosed are methods wherein the UV-irradiated radiation diagnostic composition is analyzed by ultraviolet spectrophotometer and/or HPLC at wavelength of 250, 260, 290, 326 nm or a combination of the same. In other forms, disclosed are methods wherein a representative ultraviolet absorption of TT pyrimidine (6-4) pyrimidone photolesion is at about 326 nm. In some other forms, disclosed are methods wherein a representative ultraviolet absorption of TT dinucleotide is at about 260 nm.

In some forms, disclosed are methods wherein a representative residence time of TT pyrimidine (6-4) pyrimidone photolesion in the HPLC is at about 11.2 minutes. In other forms, disclosed are methods wherein a representative residence time of TT dinucleotide in the HPLC is at about 15.9 minutes. In some forms, disclosed are methods wherein monitoring of the amount of TT pyrimidine (6-4) pyrimidone photolesion formed in the UV-irridiated radiation diagnostic composition is conducted at one or more time intervals selected from the group consisting of 0, 5, 10, 15, 20, 30, 45, 60, 75, 90, 120, 180 and 240 minutes. In some other forms, disclosed are methods wherein said efficacy of said protection composition is indicated by the amount of TT pyrimidine (6-4) pyrimidone photolesion formed in the UV-irridiated radiation diagnostic composition and/or the amount of TT dinucleotide preserved in the UV-irridiated radiation diagnostic composition.

In some forms, disclosed are methods wherein said efficacy of said protection composition as obtained from said method is consistent to SPF ranking of commercial sunscreens. In some other forms, disclosed are methods wherein said efficacy of said protection composition can be obtained without the use of human or animal subject. In some forms, disclosed are methods wherein said efficacy of said protection composition can be obtained within less than about 5, 10, 20, 30, 45, 60, 90 or 120 minutes. In some other forms, disclosed are methods wherein said testing of efficacy can be repeated with reliable results.

In some forms, disclosed are methods wherein said testing of efficacy can be cross-validated on different radiation diagnostic compositions and/or subjects. In some other forms, disclosed are methods wherein said testing of efficacy can be applied to a high-throughput screening for sunscreens. In some forms, disclosed are methods wherein said high-throughput screening for sunscreens comprises testing a plurality of sunscreens simultaneously or sequentially. In some other forms, disclosed are methods wherein said plurality of sunscreens comprises from about 5 to about 100,000 sunscreens. In some forms, disclosed are methods wherein said subject is a mammal.

Systems

Disclosed are systems comprising: (a) a first device to generate ultraviolet radiation; (b) a second device to hold one or more protection compositions; (c) a third device to contain one or more radiation diagnostic compositions representing and/or mimicing DNA in cells of a subject; and (d) a fourth device to analyze DNA damage of said radiation diagnostic composition; wherein said second device is interposed between said first device and said third device, and said third device is interposed between said second device and said fourth device.

In some forms, disclosed are systems wherein said system is useful in identifying a protection composition that reduces and/or prevents ultraviolet (UV) radiation-caused DNA damage in a subject. In some other forms, disclosed are systems wherein said first device is an ultraviolet lamp. In some other forms, disclosed are systems wherein said first device is a low-pressure mercury lamp with emission $\lambda_{max}$ about 257 nm. In some forms, disclosed are systems wherein said second device is a photolysis tube. In some other forms, disclosed are systems wherein said second device is a photolysis tube having a quartz filter with 200-nm cutoff.

In some forms, disclosed are systems wherein said third device is a cuvette. In some forms, disclosed are systems wherein said fourth device is an ultraviolet spectrophotometer, High-performance liquid chromatography (HPLC), or a combination of said ultraviolet spectrophotometer and said HPLC. In some other forms, disclosed are systems wherein said radiation diagnostic composition comprises one or more single nucleoside and/or single nucleotide in deoxy- and/or ribo-series and/or deoxy-ribo hybrids where the heterocyclic amine base is A, G, C, U or T, one or more dinucleotide in deoxy- and/or ribo-series where the heterocyclic amine base of each of the nucleotide of the dinucleotide is independently selected from a group consisting of A, G, C, U and T, one or more oligonucleotides in deoxy- and/or ribo-series where the number of the nucleotide (nt) forming the oligonucleotide is from 3 to 100 and where the heterocyclic amine base of each of the nucleotide of the oligonucleotide is independently selected from a group consisting of A, G, C, U and T, an artificial skin culture, or a combination of the same. In some other forms, disclosed are systems wherein said radiation diagnostic composition comprises one or more dinucleotides in deoxy- and/or ribo-series. Said dinucleotide comprise thymidine-thymidine (TT), thymidine-cytidine (TC), thymidine-guanosine (TG), thymidine-adenosine (TA), thymidine-uridine (TU), uridine-uridine (UU], uridine-thymidine (UT), cytidine-cytidine (CC), cytidine-adenosine (CA), guanosine-guanosine (GG), guanosine-adenosine (GA), adenosine-adenosine (AA), or adenosine-cytidine (AC) dinucleotide.

Compositions

Disclosed are radiation diagnostic compositions comprise one or more single nucleoside and/or single nucleotide in deoxy- and/or ribo-series and/or deoxy-ribo hybrids where the heterocyclic amine base is A, G, C, U or T, one or more dinucleotide in deoxy- and/or ribo-series where the heterocyclic amine base of each of the nucleotide of the dinucleotide is independently selected from a group consisting of A, G, C, U and T, one or more oligonucleotides in deoxy- and/or ribo-series and/or deoxy-ribo hybrids where the number of the nucleotide (nt) forming the oligonucleotide is from 3 to 100 and where the heterocyclic amine base of each of the nucleotide of the oligonucleotide is independently selected from a group consisting of A, G, C, U and T, an artificial skin culture, or a combination of the same, which is/are dissolved in a suitable solvent with a suitable concentration. In some forms, disclosed are radiation diagnostic compositions wherein said radiation diagnostic compositions comprising one or more dinucleotides in deoxy- and/or ribo-series and/or deoxy-ribo hybrids. Said dinucleotide comprise thymidine-thymidine (TT), thymidine-cytidine (TC), thymidine-guanosine (TG), thymidine-adenosine (TA), thymidine-uridine (TU), uridine-uridine (UU], uridine-thymidine (UT), cytidine-cytidine (CC), cytidine-adenosine (CA), guanosine-guanosine (GG), guanosine-adenosine (GA), adenosine-adenosine (AA), or adenosine-cytidine (AC) dinucleotide.

In some forms, disclosed are compositions wherein said suitable solvent is water, acetonitrile, or a mixture of water and acetonitrile with a suitable volume ratio. In other forms, disclosed are compositions wherein said suitable solvent is a mixture of water and acetonitrile wherein the volume ratio between water and acetonitrile is from about 1:20 to about 20:1. In some other forms, disclosed are compositions wherein said suitable solvent is a mixture of water and acetonitrile wherein the volume ratio between water and acetonitrile is from about 1:9 to about 9:1. In other forms, disclosed are compositions wherein said suitable solvent is a mixture of water and acetonitrile wherein the volume ratio between water and acetonitrile is about 1:9. In some other forms, disclosed are compositions wherein said suitable concentration is from about 0.01 mmol/L to about 0.5 mmol/L. In still some other forms, disclosed are compositions wherein said suitable concentration is about 0.05 mmol/L. In some other forms, disclosed are compositions wherein said composition can mimic DNA in cells of a subject and be used as a substrate in testing efficacy of one or more formulations in reducing and/or preventing from ultraviolet radiation (UV) caused DNA damage of said subject.

Definitions

A. A, an, the

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

B. Cell

The term "cell" as used herein also refers to individual cells, cell lines, or radiation diagnostic compositions derived from such cells. A "culture" refers to a composition comprising isolated cells of the same or a different type. The term co-culture is used to designate when more than one type of cell are cultured together in the same dish with either full or partial contact with each other.

C. Compound

For the purposes of the present disclosure the terms "compound," "analog," and "composition of matter" stand equally well for the chemical entities described herein, including all enantiomeric forms, diastereomeric forms, salts, and the like, and the terms "compound," "analog," and "composition of matter" are used interchangeably throughout the present specification.

D. Comprise

Throughout the description and claims of this specification, the word "comprise" and variations of the word, such as "comprising" and "comprises," means "including but not limited to," and is not intended to exclude, for example, other additives, components, integers or steps.

E. Components

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific form or combination of forms of the disclosed methods.

F. Control

The terms "control" or "control levels" or "control cells" are defined as the standard by which a change is measured, for example, the controls are not subjected to the experiment, but are instead subjected to a defined set of parameters, or the controls are based on pre- or post-treatment levels. They can either be run in parallel with or before or after a test run, or they can be a pre-determined standard.

G. Higher

The terms "higher," "increases," "elevates," or "elevation" or like terms or variants of these terms, refer to increases above basal levels, e.g., as compared a control. The terms "low," "lower," "reduces," "decreases" or "reduction" or variation of these terms, refer to decreases below basal levels, e.g., as compared to a control. For example, basal levels are normal in vivo levels prior to, or in the absence of, or addition of an agent such as an agonist or antagonist to activity. For example, decreases or increases can be used to describe the binding of a molecule to a receptor. In this context, decreases would describe a situation of where the binding could be defined as having a Kd of $10^{-9}$ M, if this interaction decreased, meaning the binding lessened, the Kd could decrease to $10^{-6}$ M. It is understood that wherever one of these words is used it is also disclosed that it could be 1%, 5%, 10%, 20%, 50%, 100%, 500%, or 1000% increased or decreased from a control.

H. Inhibit

By "inhibit" or other forms of inhibit means to hinder or restrain a particular characteristic. It is understood that this is typically in relation to some standard or expected value, in other words it is relative, but that it is not always necessary for the standard or relative value to be referred to. For example, "inhibits phosphorylation" means hindering or restraining the amount of phosphorylation that takes place relative to a standard or a control.

I. Maintaining

The word "maintaining" or like words refers to continuing a state. In the context of a treatment, maintaining can be refer to less than 20%, 15%, 10%, 9%, 8%, 7%, 6%, 5%, 4%, 3%, 2%, 1%, or 0.1% change from a control, such a basal level, often a level in the absence of a treatment or in the presence of treatment with a placebo or standard.

J. Material

Material is the tangible part of something (chemical, biochemical, biological, or mixed) that goes into the makeup of a physical object.

K. Modulate

The term modulate or like terms refers to its standard meaning of increasing or decreasing.

L. Substance

A substance or like terms is any physical object. A material is a substance. Molecules, ligands, markers, cells, proteins, DNA and RNA can be considered substances. A machine or an article would be considered to be made of substances, rather than considered a substance themselves.

M. Molecule

As used herein, the terms "molecule" or like terms refers to a biological or biochemical or chemical entity that exists in the form of a chemical molecule or molecule with a definite molecular weight. A molecule or like terms is a chemical, biochemical or biological molecule, regardless of its size.

Many molecules are of the type referred to as organic molecules (molecules containing carbon atoms, among others, connected by covalent bonds), although some molecules do not contain carbon (including simple molecular gases such as molecular oxygen and more complex molecules such as some sulfur-based polymers). The general term "molecule" includes numerous descriptive classes or groups of molecules, such as proteins, nucleic acids, carbohydrates, steroids, organic pharmaceuticals, small molecule, receptors, antibodies, and lipids. When appropriate, one or more of these more descriptive terms (many of which, such as "protein," themselves describe overlapping groups of molecules) will be used herein because of application of the method to a subgroup of molecules, without detracting from the intent to have such molecules be representative of both the general class "molecules" and the named subclass, such as proteins. Unless specifically indicated, the word "molecule" would include the specific molecule and salts thereof, such as pharmaceutically acceptable salts.

N. Optionally

"Optional" or "optionally" means that the subsequently described event or circumstance may or may not occur, and that the description includes instances where said event or circumstance occurs and instances where it does not.

O. Prevent

By "prevent" or other forms of prevent means to stop a particular characteristic or condition. Prevent does not require comparison to a control as it is typically more absolute than, for example, reduce or inhibit. As used herein, something could be reduced but not inhibited or prevented, but something that is reduced could also be inhibited or prevented. Similarly, something could be reduced and inhibited, but not prevented. It is understood that where reduce, inhibit or prevent are used, unless specifically indicated otherwise, the use of the other two words is also expressly disclosed. Thus, if inhibits phosphorylation is disclosed, then reduces and prevents phosphorylation are also disclosed.

P. Ranges

Ranges can be expressed herein as from "about" one particular value, and/or to "about" another particular value. When such a range is expressed, some forms includes from the one particular value and/or to the other particular value. Similarly, when values are expressed as approximations, by use of the antecedent "about," it will be understood that the particular value forms some forms. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data are provided in a number of different formats, and that this data, represents endpoints and starting points, and ranges for any combination of the data points. For example, if a particular datum point "10" and a particular datum point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Q. Reduce

By "reduce" or other forms of reduce means lowering of an event or characteristic. It is understood that this is typically in relation to some standard or expected value, in other words it is relative, but that it is not always necessary for the standard or relative value to be referred to. For example, "reduces phosphorylation" means lowering the amount of phosphorylation that takes place relative to a standard or a control.

R. References

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

S. Specifically Interacts

Specifically interacts or like terms means that the interaction is beyond a background interaction. The background interaction can be determined by for example looking at the interaction with serum albumin.

T. Subject

As used throughout, by a "subject" is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human. The subject can also be a non-human.

U. Tissue

Tissue or like terms refers to a collection of cells. Typically a tissue is obtained from a subject.

V. Radiation Diagnostic Composition

A Radiation diagnostic composition is any composition which mimics the properties of a chromosome, such as an oligonucleotide. By mimics means has the property of being altered when exposed to radiation, such as UV radiation. Examples of radiation diagnostic compositions are compositions comprising one or more single nucleoside(s) and/or single nucleotide(s) in deoxy- and/or ribo-series and/or deoxy-ribo hybrids where the heterocyclic amine base is A, G, C, U or T, one or more dinucleotide in deoxy- and/or ribo-series (or mixed series) where the heterocyclic amine base of each of the nucleotide of the dinucleotide is independently selected from a group consisting of A, G, C, U and T, one or more oligonucleotides in deoxy- and/or ribo-series (or mixed series) where the number of the nucleotides (nt) forming the oligonucleotide is from 3 to 100 and where the heterocyclic amine base of each of the nucleotide of the oligonucleotide is independently selected from a group consisting of A, G, C, U and T, an artificial skin culture, or a combination of the same' compositions comprising one or more dinucleotides in a deoxy- and/or ribo-series (or mixed series and/or deoxy-ribo hybrids); compositions wherein the dinucleotide comprises thymidine-thymidine (TT), thymidine-cytidine (TC), thymidine-guanosine (TG), thymidine-adenosine (TA), thymidine-uridine (TU), uridine-uridine (UU], uridine-thymidine (UT), cytidine-cytidine (CC), cytidine-adenosine (CA), guanosine-guanosine (GG), guanosine-adenosine (GA), adenosine-adenosine (AA), or adenosine-cytidine (AC) dinucleotide.

W. Protection Composition

A protection composition is any composition that reduces the amount of DNA damage to a cell, such as a sunscreen. It is understood that a protection composition can also be a composition that is being tested for a determination as to whether it reduces the amount of DNA damage to a cell, such as a composition that is being tested as to whether it is a sunscreen.

Examples

The following examples are put forth so as to provide those of ordinary skill in the art with a complete disclosure and description of how the compounds, compositions, articles, devices, systems and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

A. Materials and General Procedures

Figure 2:
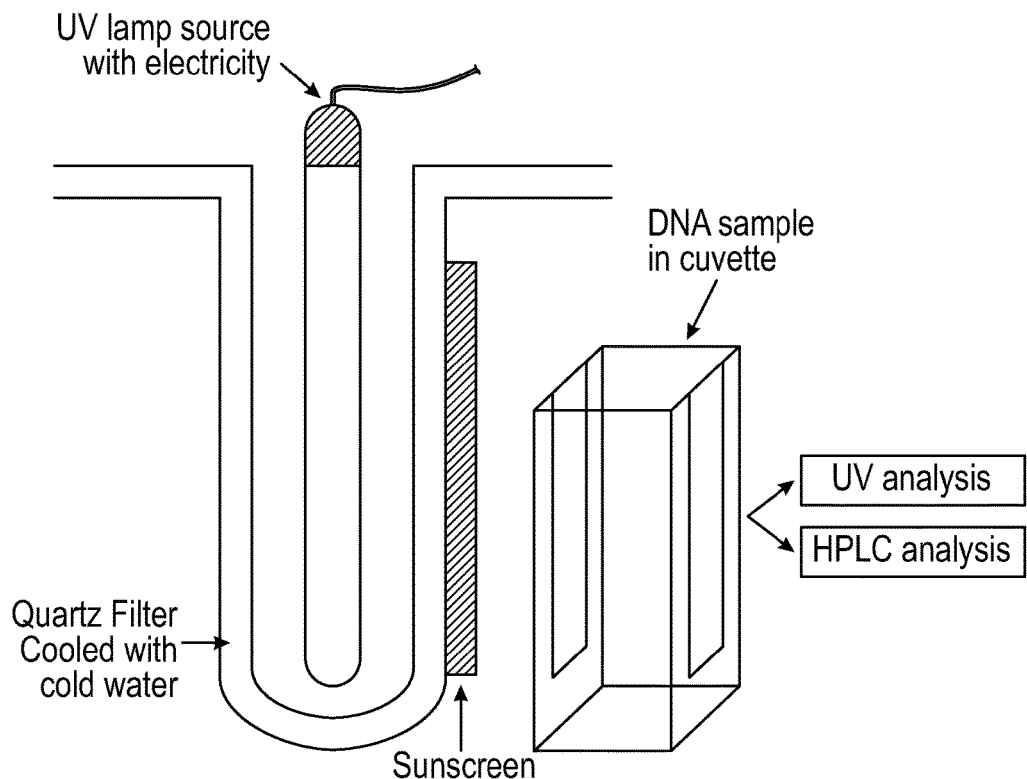
FIG. 2 shows a representative flowchart of ultraviolet (UV) irradiation of natural thymidine-thymidine dinucleotide followed by high-performance liquid chromatography (HPLC) and UV analyses.
Figure 3:
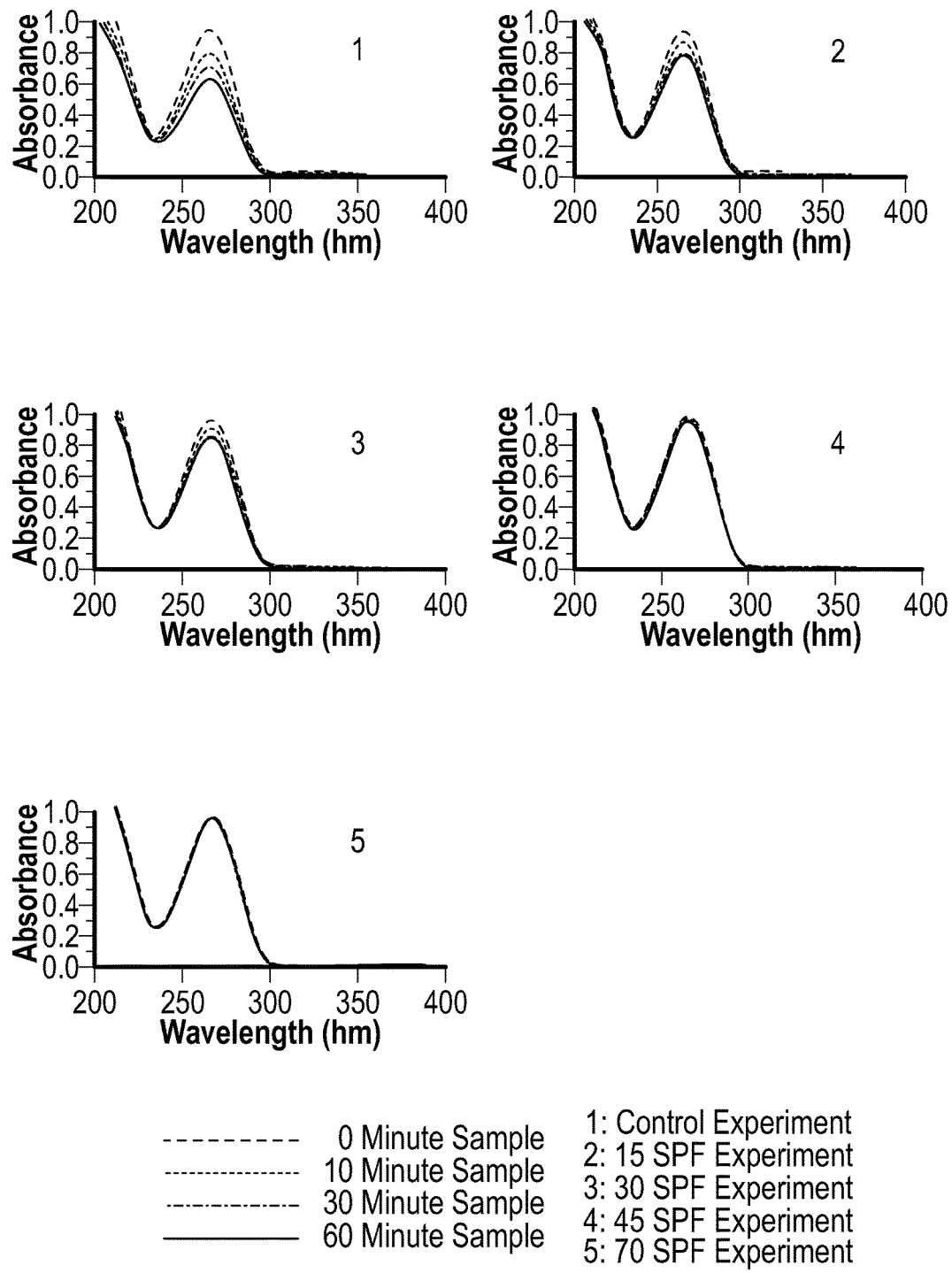
FIG. 3 shows an example of protection of thymidine-thymidine dinucleotide by sunscreens against ultraviolet (UV) damage. UV irradiation for 0, 10, 30, and 60 minutes: without sunscreen protection (control) (1); and using sunscreen with sun protection factor (SPF) 15 (2); 30 (3); 45 (4); and 70 (5).

A representative flowchart according to the present disclosure is shown in FIG. 2. Compared with other dinucleotides, the TT dinucleotide is the most sensitive to UV radiation [Marrot L, Meunier J R. Skin DNA photodamage and its biological consequences. J Am Acad Dermatol 2008; 58(Suppl):S139-48; Taylor J-S. Unraveling the molecular pathway from sunlight to skin cancer. Acc Chem Res 1994; 27:76-82; Taylor J-S, Cohrs M P. DNA, light and Dewar pyrimidinones: the structure and biological significance of TpT3. J Am Chem Soc 1987; 109:2834-5; Douki T, Court M, Cadet J. Electrospray-mass spectrometry characterization and measurement of far-UV-induced thymine photoproducts. J Photochem Photobiol B 2000; 54:145-54; Rochette P J, Therrien J P, Drouin R, Perdiz D, Bastien N, Drobetsky E A, et al. UVA-induced cyclobutane pyrimidine dimers form predominantly at thymine-thymine dipyrimidines and correlate with the mutation spectrum in rodent cells. Nucleic Acids Res 2003; 31:2786-94; Glas A F, Schneider S, Maul M J, Hennecke U, Carell T. Crystal structure of the T(6-4)C lesion in complex with a (6-4) DNA photolyase and repair of UV-induced (6-4) and Dewar photolesions. Chemistry 2009; 15:10387-96]. To mimic sunlight effects, a low-pressure mercury lamp (UVP, Ace Glass Inc, Upland, Calif.) was used. In the experiments, TT dinucleotide, dissolved in acetonitrile and water (9:1), was radiated. The mixture of the organic and water solvents mimics a biological environment where large quantities of organic molecules are present. Moreover, the effectiveness of different sunscreens with various SPFs was evaluated. Subsequently, the irradiated samples were analyzed by HPLC and UV to investigate the DNA lesion formation.

TT dinucleotide was synthesized at 10 µmol scale on an ABI 392 DNA synthesizer, followed by HPLC purification. DNA concentration studies suggested that a lower concentration generates the most lesion formation under UV irradiation. Thus, a solution of TT dinucleotide, i.e., 0.05 mmol/L in acetonitrile/water (90:10) was used for all irradiation experiments. Irradiation experiments were designed so that the sun's UV damage on DNA was mimicked by using the UV damage produced by the mercury lamp on the synthesized TT dinucleotide. A round photolysis tube, which contains a quartz filter with 200-nm cutoff, was used to hold the low-pressure mercury lamp (emission $\lambda_{max}$=257 nm). This lamp and filter setting was chosen because the TT photodimer is the major photolesion product of the sun's UV irradiation (or damage) and the TT dinucleotide is most sensitive to the UV radiation around 260 nm, leading to maximal TT photodamage. Thus, this setting was selected to mimic intensified sunlight to amplify the sun's UV damaging effect and to easily and quickly monitor the sunscreen protective effect via reduction of the TT dimer formation.

The sunscreens were applied directly on the surface of the photolysis tube, and each sunscreen (i.e., about 50 mg) was applied evenly on different designated areas (same size) on the outside wall of the photolysis tube (thickness: i.e., 0.1-0.2 mm) Experiments were carried out simultaneously using, i.e., 4 to 6 sunscreens. In addition, a control experiment, where no sunscreen was applied on the photolysis tube, was also performed each time. The Semi-Micro Quartz Cells (Starna Cells Inc, Atascadero, Calif.) containing the nucleotide solutions were placed, i.e., about 0.5 cm, away from the photolysis tube. These DNA samples were then exposed to the UV radiation from the UV lamp. At various time intervals, the UV-irradiated samples were collected and analyzed using the Cary 300 Bio UV-visible Spectrophotometer (Clayton South, Australia), HPLC, or both. The time intervals were, i.e., 0, 10, 30, and 60 minutes. The UV spectra (200-400 nm) were obtained for all samples with and without sunscreen protection (SPF 15, 30, 45, and 70). Moreover, to further differentiate the protection of sunscreens, the sunscreens were diluted. By diluting the sunscreens, larger differences between them can be observed. These diluted sunscreen experiments were carried out in a manner similar to the undiluted sunscreen experiments. In the dilution experiments, approximately 100 mg of sunscreen was used for dilution with 1 mL of either water or petroleum ether (depending on the solubility of the sunscreens). During the UV irradiation, the UV spectra were recorded at 0-, 10-, 30-, and 60-minute time intervals using a UV spectrophotometer.

After irradiation, the control samples that had been exposed to UV radiation for 0, 10, 30, and 60 minutes were analyzed by HPLC for the DNA lesion formation. These samples were analyzed mainly at two different wavelengths: 260 and 326 nm. To perform the HPLC analysis, the irradiated samples (100 µL, 0.05 mmol/L) were concentrated, and the volumes were adjusted to 50 µL (0.1 mmol/L), followed by injecting 20 µL into analytical HPLC (the reversed-phase HPLC column: XB-C18, 5 µm, 4.6×250 mm, Welch Materials Inc). For the analysis, two buffers were used. Mobile phase buffer A contained 10 mmol/L of triethylammonium acetate (pH 7.1), and buffer B contained 10 mmol/L of triethylammonium acetate (pH 7.1) in 50% acetonitrile. Each sample (20 µL, 0.1 mmol/L) was injected into HPLC with a gradient normally starting from 100% buffer A to 40% buffer B in 20 minutes, and the flow rate was 1.0 mL/min. Retention time for the TT dinucleotide was 15.9 minutes whereas the retention time for the lesion was approximately 11.2 minutes.

B. Example 1: Protection of Thymidine-Thymidine Dinucleotide by Sunscreens Against Ultraviolet (UV) Damage Monitored by UV Spectrometry The experiments (FIG. 3) were performed using a set of sunscreens. The control experiment (FIG. 3, 1), in which no sunscreen was applied on the photolysis tube, indicated that the UV absorbance of the dinucleotide in the solution decreases at 260 nm with an increase in the irradiation time. Meanwhile, upon the UV irradiation, the dinucleotide is severely damaged to form photolesions. Thus, as the irradiation time increases, the cross-linked TT photolesion that was monitored at 326 nm increases. Similarly, sunscreens with SPF 15, 30, 45, and 70 were examined (FIG. 3, 2 to 5). However, reduced absorbance changes in the 260 and 326 nm regions were observed for the analysis of sunscreens with higher SPF values. Moreover, when the sunscreen with SPF 70 was examined, no obvious DNA damage was observed under the irradiation conditions. Thus, the UV spectrometry analysis appears to be a suitable approach to rapidly examine the effectiveness of sunscreens.

To differentiate between the sunscreens that have high SPF values (eg, SPF≥45), the experiments using diluted sunscreens were carried out. In these experiments, the commercial sunscreens (100 mg each) were primarily dissolved in 1 mL of petroleum ether or water. Then, the diluted sunscreens were applied on the photolysis tube to perform the irradiation process. The UV absorbance was measured at 260 nm before and after the UV exposure. After the UV irradiation, the percentages of the undamaged TT dinucleotide were calculated and presented in FIG. 4. Each experiment was repeated at least 6 times.

Figure 4:
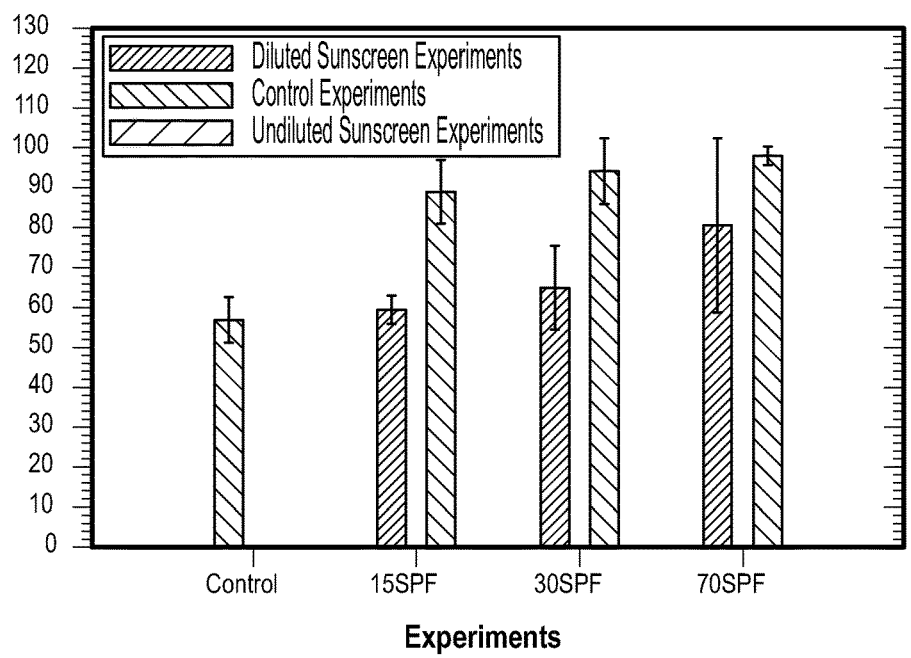
FIG. 4 shows an example of Thymidine-thymidine dinucleotide protection by sunscreens against ultraviolet (UV) damage. UV irradiation for 60 minutes in presence and absence of sunscreens (sun protection factor [SPF] 15, 30, and 70): cyan bar, Control experiment; black bar, diluted sunscreens; and gray bar, undiluted sunscreens.

In FIG. 4, the control experiment, which was performed without applying any sunscreen, is shown as the cyan bar in the bar graph. The results from the experiments using the undiluted sunscreens are presented using the gray bars. On the other hand, the results from the experiments with the sunscreen dilutions are displayed using the black bars. As shown in FIG. 4, the sunscreen protectiveness against the UV damage is reduced significantly after the dilution. Moreover, the differences in UV protection between the sunscreens become clearly demonstrable after the dilution. In principle, it should be possible to greatly differentiate between sunscreens with high SPF values, such as 60 and 70, by even further dilution. As expected, more TT dinucleotide samples survived the UV irradiation when the sunscreens with higher SPF values were used. In other words, their protectiveness ranking by the UV analysis is consistent with the SPF commercial ranking.

C. Example 2: Protection of Thymidine-Thymidine Dinucleotide by Sunscreens Against Ultraviolet (UV) Damage Monitored by High-Performance Liquid Chromatography (HPLC)

Figure 5:
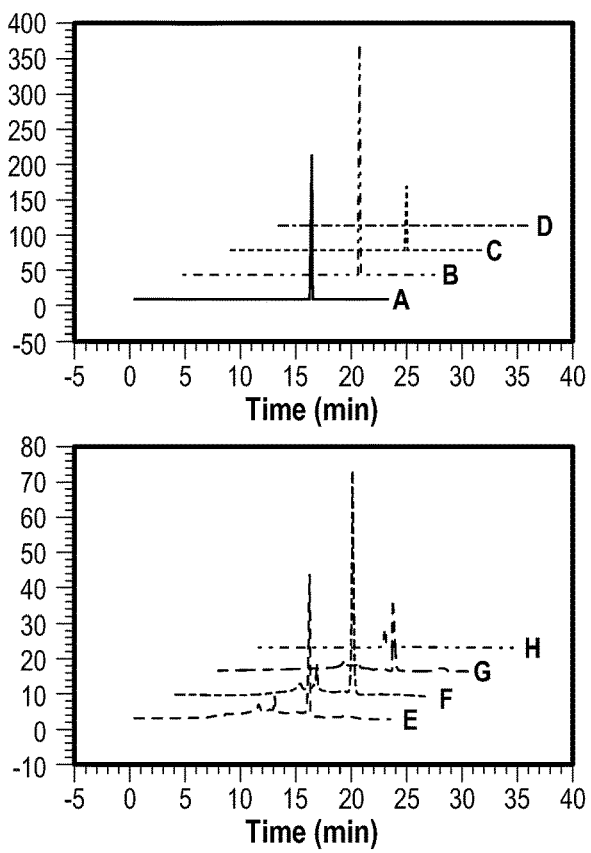
FIG. 5 shows an example of High-performance liquid chromatography (HPLC) analysis of samples without sunscreen protection before and after ultraviolet irradiation. Profiles A to D are from a sample without irradiation, monitored by HPLC at 250, 260, 290, and 326 nm, respectively. Profiles E to H are from the same sample irradiated for 60 minutes, monitored by HPLC at 250, 260, 290, and 326 nm, respectively.

In the experiments, the TT dinucleotide was used as the mimic of DNA and was irradiated under UV light. The control experiment, in which no sunscreen was applied on the photolysis tube, was performed as were the experiments with the application of sunscreens with different SPF values (15, 30, 45, and 70). The UV-irradiated samples were then analyzed by UV spectrophotometer and monitored by HPLC mainly at 4 different wavelengths: 250, 260, 290, and 326 nm. In addition, the samples were analyzed by HPLC at 4 different wavelengths before (0 minutes) and after (60 minutes) the UV irradiation. The HPLC analyses of the control samples with (for 60 minutes) and without (for 0 minutes) irradiation are shown in FIG. 5. The TT pyrimidine (6-4) pyrimidone photoproduct has a typical absorption at 326 nm [Taylor J-S. Unraveling the molecular pathway from sunlight to skin cancer. Acc Chem Res 1994; 27:76-824; Taylor J-S, Cohrs M P. DNA, light and Dewar pyrimidinones: the structure and biological significance of TpT3. J Am Chem Soc 1987; 109:2834-5]. Because of to the lesion formation, only the irradiated samples showed a peak at 326 nm. To verify this lesion formation, the control sample that was irradiated for 60 minutes was further analyzed by the coinjection with the known and synthesized (6-4) photolesion sample [Osterwalder U, Herzog B. Sun protection factors: world wide confusion. Br J Dermatol 2009; 161 (Suppl):13-24]. This HPLC analysis at 260 and 326 nm confirmed the formation of the TT (6-4) photolesion (FIG. 6).

Figure 6:
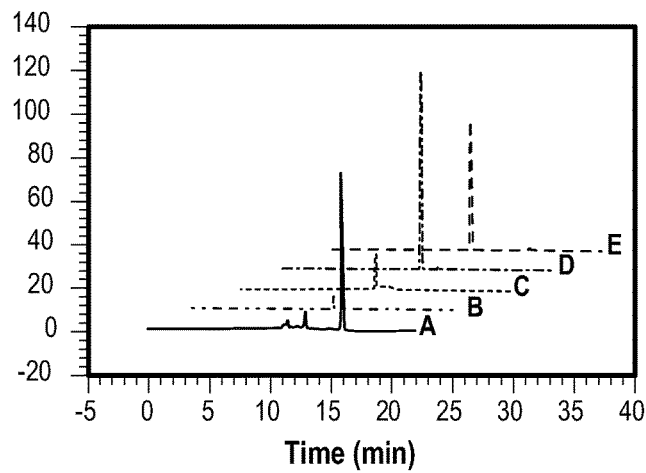
FIG. 6 shows an example of High-performance liquid chromatography (HPLC) analysis of the sample after 60-minute ultraviolet irradiation. HPLC profile of the sample monitored at 260 nm (A) and 326 nm (B). HPLC profile of thymidine-thymidine (TT) (6-4) photolesion at 260 nm (C). HPLC profile of TT (6-4) photolesion at 326 nm (D). Coinjection of the irradiated sample and TT (6-4) lesion monitored by HPLC at 326 nm (E).
Figure 7:
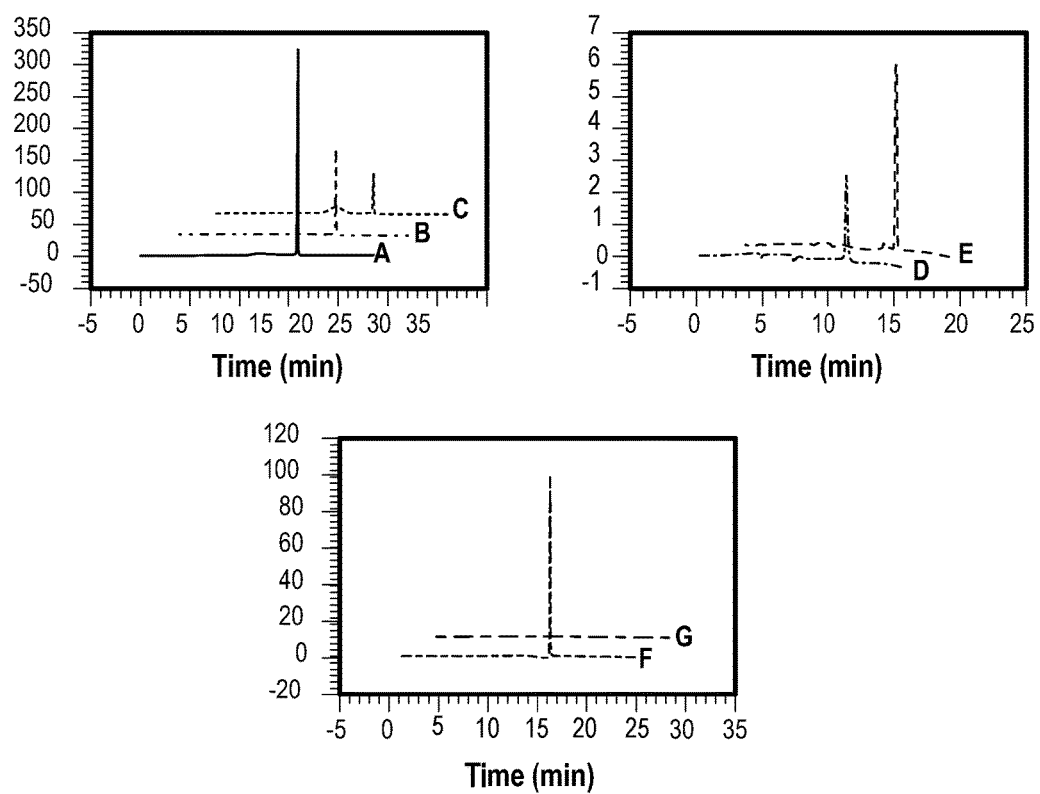
FIG. 7 shows an example of High-performance liquid chromatography (HPLC) analysis of dinucleotide samples ultraviolet irradiated in presence or absence of sunscreen. Profiles A to C are from 0-, 10-, and 60-minute, respectively, irradiated samples without sunscreen, monitored by HPLC at 260 nm. Profiles D and E are from 10- and 60-minute, respectively, irradiated samples without sunscreen, monitored by HPLC at 326 nm. Profiles F and G are from 60-minute irradiated sample protected by sun protection factor (SPF) 70, monitored at 260 nm and 326 nm, respectively. In all profiles, HPLC gradient runs from buffer A to 40% buffer B in 20 minutes.

Furthermore, HPLC is used to analyze the dinucleotide samples before and after the UV irradiation and with or without an application of sunscreen (FIGS. 5 to 7). In FIG. 7, HPLC analyses of the samples from the control experiment (profiles A to E) and the experiment using the SPF 70 sunscreen (profiles F and G) are shown. For the control experiments, the HPLC analyses of the 0-, 10-, and 60-minute UV-exposed samples analyzed at 260 nm (profiles A to C) and the 10- and 60-minute UV-exposed samples analyzed at 326 nm (profiles D and E) are presented. As the exposure time increased the native TT dinucleotide, monitored at 260 nm, decomposed and decreased (profiles A to C). At the same time, the lesion formation, which was monitored at 326 nm, increased (profiles D and E). For the experiments performed using the SPF 70 sunscreen, the HPLC analyses of the 60-minute UV-exposed sample at 260 nm (profile F) and 326 nm (profile G) are presented. Because the SPF 70 sunscreen can block the UV radiation effectively, the lesion formation was not detected. The experimental results indicate that both UV and HPLC analyses can be used to rapidly and effectively assess the protectiveness of sunscreens. Moreover, their protectiveness ranking by UV and HPLC analyses is consistent with the commercial SPF ranking.

Discussion and Summary

Disclosed are compositions comprising one or more single nucleoside and/or single nucleotide in deoxy- and/or ribo-series and/or deoxy-ribo hybrids where the heterocyclic amine base is A, G, C, U or T, one or more dinucleotide in deoxy- and/or ribo-series where the heterocyclic amine base of each of the nucleotide of the dinucleotide is independently selected from a group consisting of A, G, C, U and T (including, but not limited to, thymidine-thymidine (TT), thymidine-cytidine (TC), thymidine-guanosine (TG), thymidine-adenosine (TA), thymidine-uridine (TU), uridine-uridine (UU], uridine-thymidine (UT), cytidine-cytidine (CC), cytidine-adenosine (CA), guanosine-guanosine (GG), guanosine-adenosine (GA), adenosine-adenosine (AA), or adenosine-cytidine (AC) dinucleotide), one or more oligonucleotides in deoxy- and/or ribo-series where the number of the nucleotide (nt) forming the oligonucleotide is from 3 to 100 and where the heterocyclic amine base of each of the nucleotide of the oligonucleotide is independently selected from a group consisting of A, G, C, U and T, an artificial skin culture, or a combination of the same, dissolved in solution, i.e., the acetonitrile-water solution, can mimic DNA in cells and is sensitive to UV irradiation. Thus, it allows for the establishment of an ideal report system for studying the protectiveness of sunscreens. As a representative example of the present disclosure, on the basis of the TT reporting, it has been developed simple and rapid methods and systems via UV, HPLC or UV and HPLC for evaluation of the effectiveness of sunscreens without the use of human or animal subjects. Using this UV, HPLC, or UV and HPLC methods and systems, the effectiveness of sunscreens can be assessed easily, and the results are also consistent with the present SPF ranking of the commercial sunscreens. Moreover, as a representative example of the present disclosure, the natural TT dinucleotide is inexpensive. In addition, UV-vis and HPLC are readily available in many research and industrial laboratories. For these reasons, the disclosed methods and systems are cost-effective, convenient to perform, and allow for the establishment of quality and effectiveness cross-validation systems for comparing different sunscreen products. Furthermore, the disclosed methods and systems allow for high-throughput screening for highly efficient and non-toxic sunscreens with different ingredients. These simple and effective methods and systems for analyzing sunscreens facilitate the development of new sunscreens and help reduce cancer occurrence and/or recurrence, especially skin cancers.

REFERENCES

Nemanic M K, Whitney J, Arnaud S, Herbert S, Elias P M. Vitamin D3 production by cultured human keratinocytes and fibroblasts. Biochem Biophys Res Commun 1983; 115:444-50.

Holick M F. Sunlight and vitamin D for bone health and prevention of autoimmune diseases, cancers, and cardiovascular disease. Am J Clin Nutr 2004; 80:1678S-88S.

Marrot L, Meunier J R. Skin DNA photodamage and its biological consequences. J Am Acad Dermatol 2008; 58(Suppl):S139-48.

Taylor J-S. Unraveling the molecular pathway from sunlight to skin cancer. Acc Chem Res 1994; 27:76-82.

Taylor J-S, Cohrs M P. DNA, light and Dewar pyrimidinones: the structure and biological significance of TpT3. J Am Chem Soc 1987; 109:2834-5.

Douki T, Court M, Cadet J. Electrospray-mass spectrometry characterization and measurement of far-UV-induced thymine photoproducts. J Photochem Photobiol B 2000; 54:145-54.

Rochette P J, Therrien J P, Drouin R, Perdiz D, Bastien N, Drobetsky E A, et al. UVA-induced cyclobutane pyrimidine dimers form predominantly at thymine-thymine dipyrimidines and correlate with the mutation spectrum in rodent cells. Nucleic Acids Res 2003; 31:2786-94.

Glas A F, Schneider S, Maul M J, Hennecke U, Carell T. Crystal structure of the T(6-4)C lesion in complex with a (6-4) DNA photolyase and repair of UV-induced (6-4) and Dewar photolesions. Chemistry 2009; 15:10387-96.

Thomas M, Guillaume D, Fourrey J L, Clivio P. Further insight in the photochemistry of DNA: structure of a 2-imidazolone (5-4) pyrimidone adduct derived from the mutagenic pyrimidine (6-4) pyrimidone photolesion by UV irradiation. J Am Chem Soc 2002; 124:2400-1.

Young A R, Chadwick C A, Harrison G I, Hawk J L, Nikaido O, Potten C S. The in situ repair kinetics of epidermal thymine dimers and 6-4 photoproducts in human skin types I and II. J Invest Dermatol 1996; 106:1307-13.

Jung S K, Lee K W, Byun S, Kang N J, Lim S H, Heo Y S, et al. Myricetin suppresses UVB-induced skin cancer by targeting Fyn. Cancer Res 2008; 68:6021-9.

Shimura T, Martin M M, Torres M J, Gu C, Pluth J M, DeBernardi M A, et al. DNA-PK is involved in repairing a transient surge of DNA breaks induced by deceleration of DNA replication. J Mol Biol 2007; 367:665-80.

Ueta E, Sasabe E, Yang Z, Osaki T, Yamamoto T. Enhancement of apoptotic damage of squamous cell carcinoma cells by inhibition of the mitochondrial DNA repairing system. Cancer Sci 2008; 99:2230-7.

Brissett N C, Doherty A J. Repairing DNA double-strand breaks by the prokaryotic non-homologous end-joining pathway. Biochem Soc Trans 2009; 37:539-45.

Autier P, Boniol M, Dore J F. Sunscreen use and increased duration of intentional sun exposure: still a burning issue. Int J Cancer 2007; 121:1-5.

Sayre R M, Dowdy J C, Lott D L, Marlowe E. Commentary on 'UVB-SPF': the SPF labels of sunscreen products convey more than just UVB protection. Photodermatol Photoimmunol Photomed 2008; 24:218-20.

Young A R, Potten C S, Chadwick C A, Murphy G M, Hawk J L, Cohen A J. Photoprotection and 5-MOP photochemoprotection from UVR-induced DNA damage in humans: the role of skin type. J Invest Dermatol 1991; 97:942-8.

Bissonnette R, Alias S, Moyal D, Provost N. Comparison of UVA protection afforded by high sun protection factor sunscreens. J Am Acad Dermatol 2000; 43:1036-8.

Young A R, Sheehan J M, Chadwick C A, Potten C S. Protection by ultraviolet A and B sunscreens against in situ dipyrimidine photolesions in human epidermis is comparable to protection against sunburn. J Invest Dermatol 2000; 115:37-41.

Wagner J K, Parra E J, L Norton H, Jovel C, Shriver M D. Skin responses to ultraviolet radiation: effects of constitutive pigmentation, sex, and ancestry. Pigment Cell Res 2002; 15: 385-90.

Kelly D A, Seed P T, Young A R, Walker S L. A commercial sunscreen's protection against ultraviolet radiation-induced immunosuppression is more than 50% lower than protection against sunburn in humans. J Invest Dermatol 2003; 120: 65-71.

Dupuy A, Dunant A, Grob J J. Randomized controlled trial testing the impact of high-protection sunscreens on sun-exposure behavior. Arch Dermatol 2005; 141:950-6.

Moyal D D, Fourtanier A M. Broad-spectrum sunscreens provide better protection from solar ultraviolet-simulated radiation and natural sunlight-induced immunosuppression in human beings. J Am Acad Dermatol 2008; 58(Suppl):S149-54.

Diffey B L, Tanner P R, Matts P J, Nash J F. In vitro assessment of the broad-spectrum ultraviolet protection of sunscreen products. J Am Acad Dermatol 2000; 43:1024-35.

Wang S Q, Stanfield J W, Osterwalder U. In vitro assessments of UVA protection by popular sunscreens available in the United States. J Am Acad Dermatol 2008; 59:934-42.

Hexsel C L, Bangert S D, Hebert A A, Lim H W. Current sunscreen issues: 2007 Food and Drug Administration sunscreen labeling recommendations and combination sunscreen/insect repellent products. J Am Acad Dermatol 2008; 59:316-23.

Osterwalder U, Herzog B. Sun protection factors: world wide confusion. Br J Dermatol 2009; 161(Suppl):13-24.

Blagoev K B, Alexandrov B S, Goodwin E H, Bishop A R. Ultraviolet light induced changes in DNA dynamics may enhance TT-dimer recognition. DNA Repair (Amst) 2006; 5:863-7.

Rycyna R E, Alderfer J L. UV irradiation of nucleic acids: formation, purification and solution conformational analysis of the '6-4 lesion' of dTpdT. Nucleic Acids Res 1985; 13:5949-63.

What is claimed is:

1. A method for determining the screening efficacy of a protection composition in reducing ultraviolet (UV) radiation-caused DNA damage, the method comprising the steps of:

(a) providing ultraviolet radiation (UV);

(b) providing a radiation diagnostic composition;

(c) exposing said radiation diagnostic composition to said ultraviolet radiation which passes through a protection composition, wherein said protection composition is positioned between said radiation diagnostic composition and said ultraviolet radiation; and (d) analyzing DNA damage of said radiation diagnostic composition, wherein the step of analyzing DNA damage of said radiation diagnostic composition includes a step of monitoring the amount of TT pyrimidine (6-4) pyrimidone photolesion formed in said radiation diagnostic composition after said radiation diagnostic composition is exposed to said radiation for a predetermined period of time, wherein the step of monitoring includes the use of an ultraviolet spectrophotometer and/or high-performance liquid chromatography (HPLC) at a wavelength of 250, 260, 290, 326 nm or a combination of the same, wherein a representative ultraviolet absorption of TT pyrimidine (6-4) pyrimidone photolesion is at about 326 nm, and wherein a representative residence time of TT pyrimidine (6-4) pyrimidone photolesion in the HPLC is at about 11.2 minutes.

2. A method for determining the screening efficacy of a protection composition in reducing ultraviolet (UV) radiation-caused DNA damage, the method comprising the steps of:

(a) providing ultraviolet radiation (UV);

(b) providing a radiation diagnostic composition;

(c) exposing said radiation diagnostic composition to said ultraviolet radiation which passes through a protection composition, wherein said protection composition is positioned between said radiation diagnostic composition and said ultraviolet radiation; and (d) analyzing DNA damage of said radiation diagnostic composition, wherein the step of analyzing DNA damage of said radiation diagnostic composition includes a step of monitoring the amount of TT dinucleotide preserved in said radiation diagnostic composition after said radiation diagnostic composition is exposed to said radiation for a predetermined period of time, wherein the step of monitoring includes the use of an ultraviolet spectrophotometer and/or high-performance liquid chromatography (HPLC) at a wavelength of 250, 260, 290, 326 nm or a combination of the same, and wherein a representative ultraviolet absorption of TT dinucleotide is at about 260 nm, and wherein a representative residence time of TT dinucleotide in the HPLC is at about 15.9 minutes.

3. A method for determining the screening efficacy of a protection composition in reducing ultraviolet (UV) radiation-caused DNA damage, the method comprising the steps of:

(a) providing ultraviolet radiation (UV);

(b) providing a radiation diagnostic composition;

(c) exposing said radiation diagnostic composition to said ultraviolet radiation which passes through a protection composition, wherein said protection composition is positioned between said radiation diagnostic composition and said ultraviolet radiation; and (d) analyzing DNA damage of said radiation diagnostic composition, wherein the step of analyzing DNA damage of said radiation diagnostic composition includes a step of monitoring the amount of TT pyrimidine (6-4) pyrimidone photolesion formed in said radiation diagnostic composition after said radiation diagnostic composition is exposed to said radiation for a predetermined period of time, and wherein monitoring of the amount of TT pyrimidine (6-4) pyrimidone photolesion formed in said radiation diagnostic composition is conducted at one or more time intervals selected from the group consisting of 0, 5, 10, 15, 20, 30, 45, 60, 75, 90, 120, 180 and 240 minutes.

* * * * *